(12) United States Patent
Taube et al.

(10) Patent No.: US 9,370,535 B2
(45) Date of Patent: Jun. 21, 2016

(54) METHOD FOR TREATMENT OF ADVANCED SOLID TUMORS

(75) Inventors: Tillmann Taube, Biberach an der Riss (DE); Gerd Michael Munzert, Ulm (DE); Dorothea Rudolph, Vienna (AT)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 496 days.

(21) Appl. No.: 13/467,147

(22) Filed: May 9, 2012

(65) Prior Publication Data

US 2013/0122111 A1 May 16, 2013

(30) Foreign Application Priority Data

May 17, 2011 (EP) .................................. 11166365

(51) Int. Cl.
*A61K 31/495* (2006.01)
*A61K 31/555* (2006.01)
*A61K 33/24* (2006.01)
*A61K 31/282* (2006.01)
*A61K 31/519* (2006.01)

(52) U.S. Cl.
CPC ............... *A61K 33/24* (2013.01); *A61K 31/282* (2013.01); *A61K 31/519* (2013.01); *A61K 31/555* (2013.01)

(58) Field of Classification Search
CPC .... A61K 31/519; A61K 31/555; A61K 33/24
USPC .................................. 424/649; 514/249, 184
See application file for complete search history.

(56) References Cited

U.S. PATENT DOCUMENTS

| | | | |
|---|---|---|---|
| 4,870,175 A | 9/1989 | Suzuki et al. |
| 4,957,922 A | 9/1990 | Lammens et al. |
| 5,043,270 A | 8/1991 | Abrams et al. |
| 5,167,949 A | 12/1992 | Ferrand et al. |
| 5,198,547 A | 3/1993 | Bailey et al. |
| 5,424,311 A | 6/1995 | Billhardt-Troughton et al. |
| 5,698,556 A | 12/1997 | Chan |
| 6,096,924 A | 8/2000 | Studer et al. |
| 6,156,766 A | 12/2000 | Arita et al. |
| 6,174,895 B1 | 1/2001 | Kleinman |
| 6,605,255 B2 | 8/2003 | Kroll et al. |
| 6,806,272 B2 | 10/2004 | Bauer et al. |
| 6,861,422 B2 | 3/2005 | Hoffmann et al. |
| 6,875,868 B2 | 4/2005 | Bonnert et al. |
| 6,960,589 B2 | 11/2005 | Cowart et al. |
| 7,238,807 B2 | 7/2007 | Duran et al. |
| 7,241,889 B2 | 7/2007 | Hoffmann et al. |
| 7,332,491 B2 | 2/2008 | Grauert et al. |
| 7,371,753 B2 | 5/2008 | Stadtmueller et al. |
| 7,414,053 B2 | 8/2008 | Grauert et al. |
| 7,439,358 B2 | 10/2008 | Linz et al. |
| 7,547,780 B2 | 6/2009 | Grauert et al. |
| 7,625,899 B2 | 12/2009 | Hoffmann et al. |
| 7,626,019 B2 | 12/2009 | Duran et al. |
| 7,629,460 B2 | 12/2009 | Grauert et al. |
| 7,638,627 B2 | 12/2009 | Kankan et al. |
| 7,700,769 B2 | 4/2010 | Grauert et al. |
| 7,723,517 B2 | 5/2010 | Grauert et al. |
| 7,728,134 B2 | 6/2010 | Linz et al. |
| 7,750,152 B2 | 7/2010 | Hoffman et al. |
| 7,759,347 B2 | 7/2010 | Hoffmann |
| 7,759,485 B2 | 7/2010 | Linz et al. |
| 7,807,831 B2 | 10/2010 | Grauert et al. |
| 7,816,530 B2 | 10/2010 | Grauert |
| 8,003,786 B2 | 8/2011 | Hoffmann et al. |
| 8,034,816 B2 | 10/2011 | Linz et al. |
| 8,058,270 B2 | 11/2011 | Munzert et al. |
| 8,138,341 B2 | 3/2012 | Linz et al. |
| 8,138,373 B2 | 3/2012 | Linz et al. |
| 8,143,247 B2 | 3/2012 | Munzert et al. |
| 8,188,086 B2 | 5/2012 | Linz et al. |
| 8,193,188 B2 | 6/2012 | Hoffmann et al. |
| 8,202,867 B2 | 6/2012 | Linz et al. |
| 8,329,695 B2 | 12/2012 | Linz et al. |
| 2002/0183292 A1 | 12/2002 | Pairet et al. |
| 2002/0183293 A1 | 12/2002 | Banerjee et al. |
| 2003/0130286 A1 | 7/2003 | Denny et al. |
| 2003/0162790 A1 | 8/2003 | Cowart et al. |
| 2004/0024205 A1 | 2/2004 | Borredon et al. |
| 2004/0029885 A1 | 2/2004 | Bauer et al. |
| 2004/0127504 A1 | 7/2004 | Cowart et al. |
| 2004/0147524 A1 | 7/2004 | Bauer et al. |

(Continued)

FOREIGN PATENT DOCUMENTS

| | | |
|---|---|---|
| CA | 2458699 A1 | 3/2003 |
| CA | 2517020 A1 | 9/2004 |

(Continued)

OTHER PUBLICATIONS

Rudolph et al. BI 6727, a Polo-like kinase inhibitor with improved pharmacokinetic profile and broad antitumor activity Clin Cancer Res. May 2009.*
Schoffski et al. (Polo-Like Kinase (PLK) Inhibitors in Preclinical and Early Clinical Development in Oncology, The Oncologist 2009, 14:559-570.*
Rudolph et al. "BI 6727, A polo-like kinase inhibitor with improved pharmacokinetic profile and broad antitumor activity," Clin Cancer Res. 2009, vol. 15, No. 9, pp. 3094-3102.*
Awada et al. "Phase I trial of volasertib, a polo-like kinase inhibitor, plus platinum agents in solid tumors: safety, pharmacokinetics and activity." Invest New Drug, 2015, vol. 33, Issue 3, pp. 611-620.*
Ahlenius, T. List of cardiovascular disorder/diseases. Ahlenius, Karolinska Institutet. Stockholm, Sweden. Cardiovascular Diseases, p. 1-34, Apr. 2007.
Ahmad, N. "Polo-like kinase (Plk) 1: a novel target for the treatment of prostate cancer". The FASEB Journal. 2004, 18:5-7. Dept of Dermatology, Univ. Wisconsin, pp. 5-7.

(Continued)

*Primary Examiner* — Shengjun Wang
(74) *Attorney, Agent, or Firm* — Michael P. Morris; Atabak R. Royaee; Usha R. Patel

(57) ABSTRACT

The present invention relates to the use of Volasertib or a salt thereof or a hydrate thereof in combination with Cisplatin or Carboplatin or a salt thereof or a hydrate thereof for treating patients suffering from advanced and/or metastatic solid tumors.

8 Claims, No Drawings

(56) References Cited

U.S. PATENT DOCUMENTS

| | | |
|---|---|---|
| 2004/0176380 A1 | 9/2004 | Hoffmann et al. |
| 2005/0014760 A1 | 1/2005 | Hoffmann et al. |
| 2005/0014761 A1 | 1/2005 | Hoffmann et al. |
| 2005/0148501 A1 | 7/2005 | Palmer et al. |
| 2005/0159414 A1 | 7/2005 | Nickolaus et al. |
| 2005/0165010 A1 | 7/2005 | Nickolaus et al. |
| 2006/0004014 A1 | 1/2006 | Hoffmann et al. |
| 2006/0009457 A1 | 1/2006 | Hoffmann et al. |
| 2006/0025411 A1 | 2/2006 | Hoffmann et al. |
| 2006/0035902 A1 | 2/2006 | Linz et al. |
| 2006/0035903 A1 | 2/2006 | Mohr et al. |
| 2006/0046989 A1 | 3/2006 | Grauert et al. |
| 2006/0047118 A1 | 3/2006 | Stadtmueller et al. |
| 2006/0052383 A1 | 3/2006 | Grauert et al. |
| 2006/0058311 A1 | 3/2006 | Munzert et al. |
| 2006/0063735 A1 | 3/2006 | Redkar et al. |
| 2006/0074088 A1 | 4/2006 | Munzert et al. |
| 2006/0079503 A1 | 4/2006 | Schwede et al. |
| 2007/0043055 A1 | 2/2007 | Maier et al. |
| 2007/0117776 A1 | 5/2007 | Lyons |
| 2007/0208027 A1 | 9/2007 | Duran et al. |
| 2007/0213528 A1 | 9/2007 | Duran et al. |
| 2007/0213529 A1 | 9/2007 | Duran et al. |
| 2007/0213530 A1 | 9/2007 | Duran et al. |
| 2007/0213531 A1 | 9/2007 | Duran et al. |
| 2007/0213534 A1 | 9/2007 | Duran et al. |
| 2007/0219369 A1 | 9/2007 | Duran et al. |
| 2008/0108812 A1 | 5/2008 | Grauert et al. |
| 2008/0113992 A1 | 5/2008 | Grauert et al. |
| 2008/0171747 A1 | 7/2008 | Hoffman et al. |
| 2008/0177066 A1 | 7/2008 | Linz et al. |
| 2008/0194818 A1 | 8/2008 | Grauert et al. |
| 2008/0221099 A1 | 9/2008 | Munzert et al. |
| 2008/0293944 A1 | 11/2008 | Hoffmann et al. |
| 2008/0319190 A1 | 12/2008 | Grauert et al. |
| 2008/0319192 A1 | 12/2008 | Grauert et al. |
| 2008/0319193 A1 | 12/2008 | Grauert et al. |
| 2009/0018333 A1 | 1/2009 | Grauert et al. |
| 2009/0023733 A1 | 1/2009 | Cage et al. |
| 2009/0029990 A1 | 1/2009 | Maier et al. |
| 2009/0030004 A1 | 1/2009 | Linz et al. |
| 2009/0124628 A1 | 5/2009 | Hoffmann et al. |
| 2009/0143379 A1 | 6/2009 | Mohr et al. |
| 2009/0238828 A1 | 9/2009 | Munzert et al. |
| 2009/0280115 A1 | 11/2009 | Maier et al. |
| 2009/0298840 A1 | 12/2009 | Linz et al. |
| 2009/0306101 A1 | 12/2009 | Solca et al. |
| 2010/0029642 A1 | 2/2010 | Hoffmann et al. |
| 2010/0179134 A1* | 7/2010 | Singh et al. ............... 514/224.2 |
| 2010/0249412 A1 | 9/2010 | Linz et al. |
| 2010/0249458 A1 | 9/2010 | Linz et al. |
| 2010/0280037 A1 | 11/2010 | Linz et al. |
| 2010/0324288 A1 | 12/2010 | Hoffmann et al. |
| 2011/0046176 A1 | 2/2011 | Moore, II et al. |
| 2012/0107312 A1 | 5/2012 | Munzert et al. |
| 2012/0214995 A1 | 8/2012 | Linz et al. |
| 2012/0238754 A1 | 9/2012 | Schnaubelt et al. |
| 2012/0295864 A1 | 11/2012 | Taube et al. |
| 2012/0296091 A1 | 11/2012 | Sieger et al. |
| 2012/0329803 A1 | 12/2012 | Linz et al. |
| 2013/0012465 A1 | 1/2013 | Haslinger et al. |

FOREIGN PATENT DOCUMENTS

| | | |
|---|---|---|
| CA | 2517010 A1 | 11/2004 |
| CA | 2576290 A1 | 2/2006 |
| EP | 143478 A1 | 6/1985 |
| EP | 347146 A2 | 12/1989 |
| EP | 399856 A1 | 11/1990 |
| EP | 429149 A1 | 5/1991 |
| ES | 2287583 | 12/2007 |
| JP | 2009169737 A | 6/1997 |
| RU | 2002125451 A | 1/2004 |
| WO | 9608537 A1 | 3/1996 |
| WO | 9609045 A1 | 3/1996 |
| WO | 9634867 A1 | 11/1996 |
| WO | 9636597 A1 | 11/1996 |
| WO | 9811893 A1 | 3/1998 |
| WO | 0119825 A1 | 3/2001 |
| WO | 0170741 A1 | 9/2001 |
| WO | 0178732 A1 | 10/2001 |
| WO | 02057261 A2 | 7/2002 |
| WO | 02076954 A1 | 10/2002 |
| WO | 02076985 A1 | 10/2002 |
| WO | 03020722 A1 | 3/2003 |
| WO | 03093249 A1 | 11/2003 |
| WO | 2004014899 A1 | 2/2004 |
| WO | 2004024728 A2 | 3/2004 |
| WO | 2004076454 A1 | 9/2004 |
| WO | 2004093848 A2 | 11/2004 |
| WO | 2005067935 A1 | 7/2005 |
| WO | 2006005510 A1 | 1/2006 |
| WO | 2006018182 A1 | 2/2006 |
| WO | 2006018185 A2 | 2/2006 |
| WO | 2006018220 A2 | 2/2006 |
| WO | 2006018221 A1 | 2/2006 |
| WO | 2006021378 A1 | 3/2006 |
| WO | 2006021379 A1 | 3/2006 |
| WO | 2006021547 A1 | 3/2006 |
| WO | 2007014838 A1 | 2/2007 |
| WO | 2007054551 A1 | 5/2007 |
| WO | 2007090844 A1 | 8/2007 |
| WO | 2009019205 A1 | 2/2009 |
| WO | 2009112524 A1 | 9/2009 |
| WO | 2010111172 A1 | 9/2010 |
| WO | 2011101369 A1 | 8/2011 |
| WO | 2012049153 A1 | 4/2012 |
| WO | 2012072505 A1 | 6/2012 |
| WO | 2012156283 A1 | 11/2012 |
| WO | 2012156380 A1 | 11/2012 |

OTHER PUBLICATIONS

Arnold, K. "Collaboration to play key role in NCI's future, director says". Journal of the National Cancer Institute, Jun. 5, 2002, pp. 790-792, vol. 94, No. 11.

BBC News/Health, Killer Breast Cancern Therapy Hope, www.newsvote.bbc/co./uk, Published Jan. 21, 2006.

Bennett, J.C., et al., "Textbook of Medicine", Part XIV Oncology, 1997.

Blain, S. W. et al., "Differential interaction of the cyclin-dependent kinase (Cdk) Inhibitor p27KIP with cyclin A-Cdk2 and cyclin D2-Cdk4". The Journal of Biological Chemistry, vol. 272, No. 41, Issue Oct. 10, 1997, pp. 25862-25872.

Bug, G. et al., "Phase I/II Study of BI6727 (volasertib), n Intravenous Polo-Like Kinase-1 (Plk1) Inhibitor, in Patients with Acute Myeloid Leukemia (AML): Results of the Dose Finding for BI 6727 in Combination with Low-dose Cytarabine". Blood, vol. 116, No. 21, Nov. 19, 2010, p. 1359, American Socieity of Hematology (ASH); Orlando, FL, Dec. 2010.

Chen, J.X. et al., "Parallel differentiated recognition of ketones and acetals". Angewandte Chemie Int. Ed, vol. 37, Issue 1/2, p. 91-93, 1998.

Eurasian Opinion, Appln No. 2007/00389/28, Maly Slatoustinsky per., d.10, kv.15, 101000 Moscow, Russia, "EVROMARKPAT", 2007.

Ghandi, L., et al., "An Open-Label Phase II Trial of the PLK Inhibitor BI 2536 in Patients with Sensitive Relapse Small Cell Lung Cancer". ASCO Meeting 2009.

Goodman-Gilman's "The Pharmacological Basis of Therapeutics". Ninth edition, 1996, pp. 1225-1271.

Ito, Y., et al., "Polo-like kinase 1 (PLK) expression is associated with cell proliferative activity and cdc2 expression in malignant-lymphoma of the thyroid". Anticancer Research, 2004, vol. 24, No. 1, pp. 259-263.

Jaworska, J., et al., "Review of methods for assessing the applicability domains of SARS and QSARS". Sponsor: The European Commission—Joint Research Ctr., Institute for Health and Consumer Protection—ECVAM, Italy, 2004.

Kashima, M. K. et al., "Expression of polo-like kinase (PLK1) in non-Hodgkin's lymphomas". NCBI, PubMed, 2005.

(56) References Cited

OTHER PUBLICATIONS

Kimball, S. D. et al., "Cell cycle kinases and checkpoint regulation in cancer". Annual Reports in Medicinal Chemistry, 36, Chapter 14, 2001, pp. 139-148.
Kummer B, et al., "Combination of Radiation and Polo-like Kinase 1 Inhibition with BI6727 in tumour model A431". Vortrag. 20. Symposium „Experimentelle Strahlentherapie and klinische Strahlenbiologie, Exp. Strahlenther. Klin. Strahlenbiol. 20: 93-96 (2011) (Lecture 20, Symposium Experimental Radiation Therapy and Clinical Radiation Biology.).
Kummer, B. et al., Presentation: "Combination of irradiation and polo-like kinase 1 inhibition with BI 6727 in tumour model A 431". OncoRay—National Centre for Radiation Research in Oncology, Dresden 2011, Experimental Radiotherapy and Clinical Radiobiology.
Leukemia & Lymphoma Society—Disease Information-Lymphoma. www.leukemia-lymphoma.org/all_page?item_id-7030, 2008.
Leukemia & Lymphoma Society—Disease Information. www.leukemia-lymphoma.org/all_page?item_id-7026, 2008.
Marko, D. et al., "Intracellular localization of 7-benzylamino-6-chloro-2-piperazino-4-pyrrolidino-pteridine in membrane structures impeding the inhibition of cytosolic cyclic AMP-specific phosphodiesterase". Biochemical Pharmacology, 63, 2002, pp. 669-676.
Mashkovkii, M.D., "Medicaments". Moscow, Novaja Volna, 2001, vol. 1, p. 11.
Mashkovskii, M.D. "Drugs", Handbook for Doctors, 1993, Part I, Ch.1, p. 8.
Masuda, Y. et al., "B-Hydroxyisovalerylshikonin induces apoptosis in human leukemia cells by inhibiting the activity of a polo-like kinase 1 (PLK)". 2003, Oncogene, 22, pp. 1012-1023.
Mayer, SF, et al., "Enzyme-initiated domino (cascase) reactions". Chem. Soc. Rev, 2001, p. 332-339.
MedlinePlus: Bacterial Infections. www.nim.nih.gov/medlineplus/print/bacterialinfections.htm, date last updated Mar. 25, 2009.
MedlinePlus: Viral Infections. www.nim.nih.gov/medlineplus/print/viralinfections.htm, date last updated Feb. 11, 2009.
Merck Manual of Medical Information—Home Edition, Section 17. "Parasitic Infections". Chapter 184, 2003.
Mikhailov, I.B., Principles of Rational Pharmacotherapy. Handbook for clinical pharmacology for students of pediatric and medical faculties of medical high schools, St. Petersburg, Russia, "Foliant", 1999, p. 25.
Mito, K., et al., "Expression of polo-like kinase (PLK1) in non-Hodgkin's lymphomas". NCBI, PubMed, 2005, Leuk. Lymphoma, 46(2), pp. 251-231.
Nagao, K. et al., "Effect of MX-68 on airway inflammation and hyperresponsiveness in mice and guinea-pigs". Journal of Pharmacy and Pharmacology, JPP 2004, 56, pp. 187-196.
National Institute of Neurological Disorders, Index Stroke, 2006.
Neidle, S. ed., "Cancer Drug Design and Discovery", Elsevier/Academic Press, 2008, p. 427-431.
Norman, P. "PDE4 inhibitors". Ashley Publications Ltd., Expert Opinions Ther. Patents, 1999, pp. 1101-1118.
Office Action mailed Dec. 10, 2003 for U.S. Appl. No. 10/226,710, filed Aug. 23, 2002. Inventor: Eckhart Bauer.
Office Action mailed Apr. 28, 2004 for U.S. Appl. No. 10/374,876, filed Feb. 26, 2003. Inventor: Matthias Hoffmann.
Ohio Dept of Health, "Brain and Other Central Nervous System Cancer in Ohio, 1997-2001". Sep. 2004, pp. 1-4.
Organic Chemistry, Grupo Editorial Iberoamerica, Section 13, 3, pp. 301-302, 1983 (best copy available in Spanish).
Rocha Lima, C.M. et al. "Randomized phase II trial of gemcitabine plus irinotecan or docetaxel uin stage IIIB or stage IV NSCLC" Annals of Oncology, 15(3), p. 410-418, 2004.
Rudolph, D. et al., "430 Poster Characterization of BI 6727, a novel Polo-like kinase inhibitor with a distinct pharmacokinetic profile and efficacy in a model of taxane-resistant colon cancer". European Journal of Cancer. Supplement, Pergamon, Oxford, GB, vol. 6, No. 12, Oct. 1, 2008, p. 135. [retrieved on Oct. 1, 2008].

Santing, R. E. et al., "Brochodilatory and anti-inflammatory properties of inhaled selective phosphodiesterase inhibitors in a guinea pig model of allergic asthma". European Journal of Pharmacology, 429, 2001, pp. 335-344.
Science, vol. 310, Oct. 21, 2005, p. 409, Chemistry: One After Another.
Snyder, J. S. et al., "Common bacteria whose susceptibility to antimicrobials is no longer predictable". NCBI, PubMed, 2000, Le Journal Medical Libanais (The Lebanse Medical Journal), 48, pp. 208-214.
Sugar, A. M. et al., "Comparison of three methods of antifungal susceptibility testing with the proposed NCCLS standard broth macrodilution assay: lack of effect of phenol red". Mycology, Diagn Microbiol. Infect. Dis. 1995, 21—pp. 129-133.
Takai, N. et al., "Polo-like kinases (PLKs) and cancer". Oncogene, 2005, 24, pp. 287-291.
Tenbrink, R. E. et al., "Antagonist, partial agonist, and full agonist imidazo[1,5-a]quinoxaline amides and carbamates acting through the BABA/Benzodiazepine receptor". J. Med. Chem. 1994, 37, pp. 758-768.
Turner, W.W.et al., "Recent advances in the medicinal chemistry of antifungal agents". Current Pharmacutical Design, 1996, 2, pp. 209-224.
Verschuren, E.W. et al., "The cell cycle and how it is steered by Kaposi's sarcoma-associated herpesvirus cyclin". Journal of General Virology, 2004, 85, pp. 1347-1361.
Voskoglou-Nomikos, T. et al., "Clinical predictive value of the in vitro cell line, human xenograft, and mouse allograft preclinical cancer models". Clinical Cancer Research vol. 9, 2003, pp. 4227-4239.
Wagner, B. et al, "7-Benzylamino-6-chloro-2-piperazino-4-pyrrolidino-pteridine, a potent inhibitor of cAMP-specific phosphodiesterase, enhancing nuclear protein binding to the CRE consensus sequence in human tumour cells", Biochemical Pharmacology, Pergamon, Oxford, GB, 2002, pp. 659-668.
Wolf, D. E.et al., "The structure of rhizopterin". Contribution from the Research Labs of Merck and Co. Inc. Nov. 1947, Journal of American Chem. Soc., vol. 69, pp. 2753- 2759. XP002352205.
Rylander, P.N. "Hydrgenation Methods". 1985, Chapter 5, 6, 7.
Rylander, P.N., "Hydrogenation Methods". 1985, Chapters 1, 2.
Savelli, F. et al., "Heterotricyclic system Part II—synthesis of new pyrido[1'2':4,5]pyrazino[3,2-d] pyrimidines". Bollettino Chimico Farmaceutico, 131(8), Sep. 1992, pp. 309-312.
Seetharam, M. et al., "Treatment of higher risk myelodysplastic syndrome patients unresponsive to hypomethylating agents with ON 01910.Na." Leukemia Research, 2012, vol. 36, pp. 98-103.
Serajuddin, Abu T.M., "Salt formation to improve durg solubility", Advanced Drug Delivery Reviews, 59, 2007, 603-616.
Souillac, P. et al., "Characterization of delivery systems, differential scanning calorimetry". (In Encyclopedia of Controlled Drug Delivery), 1999, John Wiley & Sons, pp. 212-227.
Turner, S., "The Design of Organic Syntheses". Elsevier, 1976, pp. 10 and 149.
Vippagunta, S. R. et al., "Crystalline solids". Advanced Drug Delivery Reviews, 48, 2001, pp. 3-26.
Visiting Nurse Association of America. www.vnaa.org/gen/Germ_Protection_Center_Cold_and_Flu_Resources,html, 2009.
Wagner, G. et al. "Synthesis of new phrido[3',2':4,5] thieno '3,2-d] 1,2,3-triazine derivatives as antianaphylactics". Biosciences Dept of the University of Leipzig, Pharmazie (Pharmacy), 48, vol. 7,1993, pp. 514-518.
Webster's Comprehensive Dictionary, 1996, pp. 1013-1014.
Wikipedia. "Melting Point", Jan 17, 2007. http://en.wikipedia.org/wiki/Melting_point.
X-ray Diffraction—Factors that affect d's and I's. [Downloaded from the internet Mar. 9, 2011, URL: http://www.gly.uga.edu/Schroeder/geol6550/XRD.html].
Berg, T. et al., "Polo-like kinases in AML" Expert Opinion on Investigational Drugs, 2012, vol. 21, No. 8, pp. 1069-1074.
Boulikas, T. et al., "Recent clinical trials using cisplatin, carboplatin and their combination chemotherapy drugs (Review)." Oncology Reports, 2004, vol. 11, pp. 559-595.

(56) References Cited

OTHER PUBLICATIONS

Bug, G. et al., "Phase I/II Study of BI 6727 (volasertib), An Intravenous Polo-Like Kinase-1 (Plk1) Inhibitor, In Patients with Acute Myeloid Leukemia (AML): Results of the Dose Finding for BI 6727 in Combination with Low-Dose Cytarabine." Blood, 2010, vol. 116, pp. 1-2.
Clinical Trials: NCT01348347. B16727 (Volasertib) Monotherapy Phase I Trial in Japanese Patients with Advanced Soliid Tumours. Apr. 29, 2011 [Retrieved from the Internet: URL: http://www.clinicaltrials.gov./ct2/show/NCT01348347?term=volasertib&rank=1] retrieved Jul. 16, 2012.
Ellis, P.M. et al., "A Phase I Open-Label Dose-Escalation Study of Intravenous BI 2536 Together with Pemetrexed in Previously Treated Patients with Non-Small-Cell Lung Cancer" Clinical Lung Cancer, 2012, p. 1-9.
Gil, T. et al., "Final analysis of a phase I single dose-escalation study of the novel polo-like kinase 1 inhibitor BI 6727 in patients with advanced solid tumors." 2010 ASCO Annual Meeting, Journal of Clinical Oncology, Poster Abstract No. 3061.
International Search Report and Written Opinion for PCT/EP2011/071008 mailed Feb. 28, 2012.
International Search Report and Written Opinion for PCT/EP2012/058704 mailed Aug. 8, 2012.
International Search Report and Written Opinion for PCT/EP2014/065937 mailed Oct. 6, 2014.
International Search Report and Written Opinion for PCT/EP2014/065938 mailed on Sep. 9, 2014.
Lin, C-C et al., "A phase I study of two dosing schedules of volasertib (BI 6727), an intravenous polo-like kinase inhibitor, in patients with advanced solid malignancies." British Journal of Cancer, 2014, pp. 1-7.
Medema et al.; Polo-like Kinase 1 Inhibitors and Their Potential Role in Anticancer Therapy, with a Focus on NSCL; Clinical Cancer Research; 2011; vol. 17; No. 20; pp. 6459-6466.
Mross, K. et al., A randomised phase II trial of the polo-like kinase inhibitor BI 2536 in chemo-naieve patients with unresectable exocrine adenocarcinoma of the pancreas—a study within the Central European Society Anticancer Drug research (CESAR) collaaborative work. British Journal of Cancer, 2012, p. 1-7.
Phys. Org. "New way of inhibiting cell cycle shows promise." Oct. 22, 2008, pp. 1-2. http://phys.org/news143890171.html.
Schoffski, P. et al., "A phase I, dose-escalation study of the novel Polo-like kinase inhibitor volasertib (BI 6727) in patients with advanced solid tumors." European Journal of Cancer, 2012, vol. 48, pp. 179-186.
Schoffski, P., "Polo-like kinase (PLK) inhibitors in preclinical and early clinical development in oncology", The Oncologist, vol. 14, 2009, pp. 559-570.
Schoffski, P., et al., "A phase I single dose escalation study of the novel polo-like kinase 1 inhibitor BI 6727 in patients with advanced solid tumours", EJC Supplement, vol. 6. No. 12, Oct. 2008, p. 14-15.
Xu, W-J., "Efficient Inhibition of Human Colorectal Carcinoma Growth by RNA Interference Targeting Polo-Like Kinase 1 In Vitro and In Vivo." Cancer Biotherapy and Radiopharmaceuticals, 2011, vol. 26, No. 4, pp. 427-436.
"Salt Forms of Drug Absorption", Swarbrick, et al. editors, Encyclopedia of Pharm. Tech. 13 Marcel Dekker, NY, 1996, 453-499.
Abstract in English for JP09169737, Date of Publication: Jun. 30, 1997, Applicant Tosoh Corp, Inventor: K. Hiroyuki, Title: Production of N-Methylimidazoles. Date filed: Dec. 21, 1995.
ACPS Meeting, Background Information. "Scientific considerations of plymorphism in pharmaceutical solids: abbreviated new drug applications". Oct. 2002.
Badawy, S. I. et al., "Sale Selection for Phamaceutical Compounds", Preformulation in Solid Dosage Form Develolpment, Infoa Healthcare 2008, Chapter 2.3, 63-80.
Bastin, R. J. et al., "Salt Selection and Optimisation Procedures for Pharmaceutical New Chemical Entities", Organic Process Research and Development, 2000, 4,427-435.
Benetatos, L. et al., "Polo-like kinase 2 (SNK/PLK2) is a novel epigenetically regulated gene in acute myeloid leukemia and myelodysplastic syndromes: genetic and epigenetic interactions." Annals of Hematology, 2011, vol. 90, No. 9, pp. 1037-1045.
Beshore, D.C.et al., "Preparation of Substituted Piperazinones via Tandem Reductive Amination-N.N-Acyl Transfer)-Cyclization". Organic Letters, 2002, vol. 4, No. 7, p. 1201-1204.
Cancer Drug Design and Discovery, Stephen Neidle, Ed. (Elsevier/Academic Press, 2006), p. 427-431.
Christoph, D. et al., "Polo-like kinase 1 inhibitors in mono-and combination therapies: a new strategy for treating malignancies." Expert Review of Anticancer Therapy, 2011, vol. 11, No. 7, pp. 1115-1130.
Dipolar aprotic solvent. Exhibit A, IUPAC Compendium of Chemical Terminology, 2nd Edition, 1997.
Doerwald, F.Z. Book Wiley-VCH Verlag GmbH & Co. KGaA, "Side reactions in organice synthesis: A Guide to Successful Synthesis Design". 2005.
Dyson, G, et al. "The Chemistry of Synthetic Drugs". 1964, p. 12-19.
Expert Scientific Group on Phase One Clinical Trials, Final Report, Nov. 30, 2006, pC1, C35-C38.
Ferrand, G., et al., "Synthesis and potential antiallergic activity of new pteridinones and related compounds". Eur. J. Med. Chem, 31, 1996, pp. 273-280. XP—2246920.
Giron, G. "Thernal analysis and calorimetric methods in the characterization of plymorphs and solvates". Thermochimica Acta 248, 1995, pp. 1-59.
Goodman & Gilman's The Pharmacological Basis of Therapeutics, Tenth Edition, Chapter 1 "Pharmacokinetics: The Dynamics of Drug Absorption, Distribution, and Elimination." 2001, pp. 3-29.
Goodman and Gilman 9th Edition; 1996; pp. 1225-1232 and 1269-1271.
Gould, P. L., "Salt selection for basic drugs", International Journal of Pharmaceutics, 33(1986), 201-217.
Gura, T. "Cancer Models: Systems for Identifying New Drugs are Often Faulty". Science, Nov. 7, 1997, vol. 278, No. 5340—p. 1041-1042.
International Seach Report for PCT/EP2007/051139 mailed May 29, 2007.
International Search Report and Written Opinion for PCT/EP2005/008623 mailed Nov. 23, 2005.
International Search Report and Written Opinion for PCT/EP2005/008626 mailed Feb. 10, 2006.
International Search Report and Written Opinion for PCT/EP2008/060112 mailed Nov. 6, 2008.
International Search Report and Written Opinion for PCT/EP2011/052280 mailed Apr. 29, 2011.
International Search Report and Written Opinion for PCT/EP2011/067696 mailed Nov. 4, 2011.
International Search Report and Written Opinion for PCT/EP2014/065939 mailed Sep. 9, 2014.
International Search Report for PCT/EP03/01935 mailed Jul. 23, 2003.
International Search Report for EP2005/007347 mailed Oct. 18, 2005.
International Search Report for PCT/EP2005/006404 mailed Nov. 14, 2005.
International Search Report for PCT/EP2005/007532 mailed Oct. 6, 2005.
International Search Report for PCT/EP2005/008734. mailed Aug. 25, 2006.
International Search Report for PCT/EP2005/008735 mailed Dec. 8, 2005.
International Search Report for PCT/EP2005/008736 mailed Nov. 30, 2005.
International Search Report for PCT/EP2005/008990 mailed Dec. 13, 2005.
International Search Report for PCT/EP2005/008991 mailed Dec. 15, 2005.
International Search Report for PCT/EP2005/054096 mailed Jan. 24, 2006.
International Search Report for PCT/EP2005/054099 mailed Dec. 15, 2005.

(56) References Cited

OTHER PUBLICATIONS

International Search Report for PCT/EP2005/056291 mailed Mar. 21, 2006.
International Search Report for PCT/EP2006/064305 mailed Oct. 16, 2006.
Jamieson, C. et al., "Application of ReactArray Robotics and Design of Experiments Techniques in Optimisation of Supported Reagent Chemistry". Org. Proc. Res. & Dev., 2002, 6, pp. 823-825.
Kamb, A. "What's wrong with our cancer models?". Nature Reviews Drug Discovery, vol. 4, Feb. 2005, pp. 161-165.
Kola, I. et al., "Can the phamaceutical industry reduce attrition rates?" Nature Reviews Drug Discovery, vol. 3, Aug. 2004, pp. 711-715.
Krause, M. et al., "Combination of Radiation and Polo-like Kinase 1 Inhibition with BI 6727 in tumour model A431". Strahlenther Onkol, 187, S1, 53 (v17-6), 2011.
Leaf, C. et al., "Why are we losing the war on cancer (and how to win it)". Health Administrator, vol. XVII, No. 1, 2005, pp. 172-183.
Morris, K.R. et al., "An integrated approach to the selection of optimal salt form for a new drug candidate", International Journal of Pharmaceutics, 105, 1994, 209-217.
Neau, S. H., Pharmaceutical Salts, CRC Press, 2008, Ch 17, pp. 417-435.
Roberts, Jr., T. G. et al. "Trends in the Risks and Benefits to Patients with Cancer Participating in Phase 1 Clinical Trials". JAMA, Nov. 3, 2004, vol. 292, No. 17, pp. 2130-2140.
Rylander, P.N. "Hydrgenation Methods". 1985, Chapter 13.
Rylander, P.N. "Hydrgenation Methods". 1985, Chapters 3, 4.
Rylander, P.N. "Hydrgenation Methods". 1985, Chapters 8, 9, 10, 11.
International Search Report and Written Opinion for PCT/EP2015/072386 mailed Dec. 2, 2015.

\* cited by examiner

METHOD FOR TREATMENT OF ADVANCED SOLID TUMORS

The present invention relates to the use of Volasertib or a salt thereof or a hydrate thereof in combination with Cisplatin or Carboplatin or a salt thereof or a hydrate thereof for treating patients suffering from advanced and/or metastatic solid tumours.

BACKGROUND OF THE INVENTION

Most advanced and/or metastatic solid tumours are incurable despite the availability of a variety of established treatment modalities like surgery, cytotoxic drugs, radiation therapy, and combinations of these. Objective responses in patients with advanced disease, though frequently seen using these treatments, are often followed by tumour progression and death. Therefore the search for new therapeutic strategies has become an urgent priority.

The efficacy of chemotherapeutic agents can be improved by combining anti-cancer drugs with different mode of action as well as by improving the dosage schedule. Even if the concept of combination therapies and improved dosage schedules already has been suggested, there is still a need for new and efficient therapeutic concepts for the treatment of cancer diseases, which show advantages over standard therapies.

Volasertib is a highly potent and selective inhibitor of the serine-threonine Polo like kinase 1 (Plk1), a key regulator of cell-cycle progression. Volasertib is a dihydropteridinone derivative with distinct pharmacokinetic (PK) properties. The problem underlying this invention was to develop improved dosage schedules for combination therapy of advanced and/or metastatic solid tumours.

Volasertib (I) is known as the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide,

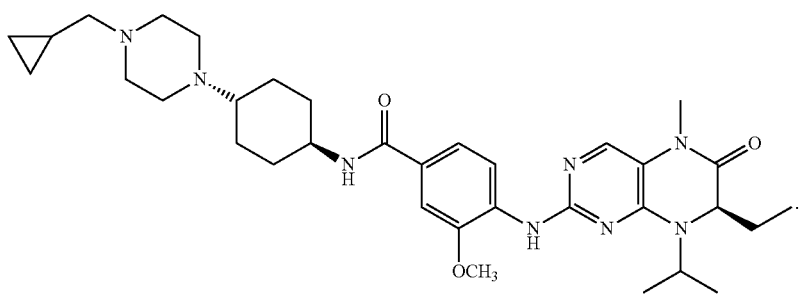

(I)

This compound is disclosed in WO 04/076454. Furthermore, trihydrochloride salt forms and hydrates thereof are known from WO 07/090844. They possess properties which make those forms especially suitable for pharmaceutical use. The above mentioned patent applications further disclose the use of this compound or its monoethanesulfonate salt for the preparation of pharmaceutical compositions intended especially for the treatment of diseases characterized by excessive or abnormal cell proliferation.

Cisplatin (cis-diamminedichloroplatinum(II) (CDDP) (trade names Platinol and Platinol-AQ) is a chemotherapy drug. It is used to treat various types of cancers, It reacts in vivo, binding to and causing crosslinking of DNA, which ultimately triggers apoptosis.

Carboplatin (cis-Diammine(1,1-cyclobutanedicarboxylato)platinum(II) (trade names Paraplatin and Paraplatin-AQ) is a chemotherapy drug used against different forms of tumours. Carboplatin interact with DNA, similar to the mechanism of alkylating agents.

DETAILED DESCRIPTION OF THE INVENTION

In clinical trials with patients suffering suffering from advanced and/or metastatic solid tumours including NSCLC (non small cell lung cancer), sarcoma, colorectal cancer and melanoma it has been found that high dosages of Volasertib or a salt thereof or a hydrate thereof can be administered in combination with high dosages of cisplatin or carboplatin both having a profile of side effects (myelosuppression) which is overlapping to that of Volasertib without potentiation of those side effects.

Therefore, a first object of the present invention relates to a method of treating patients suffering from advanced and/or metastatic solid tumours characterized by the
  a) administration of 300 to 500 mg, preferably 300 or 350 mg of Volasertib or a pharmaceutically acceptable salt thereof or a hydrate thereof at one day within a 14, 15, 16, 17, 18, 19, 20, 21, 22, 23, 24, 25, 26, 27, 28, 29, 30 or 31 day treatment cycle and
  b) administration of 50 to 100 mg/m² body surface area (BSA), preferably 75 to 100 mg/m² BSA of Cisplatin at one day within the same treatment cycle,
to a patient suffering from advanced and/or metastatic solid tumours (dosage schedule I).

Another object of the invention relates to a method of treating patients suffering from advanced and/or metastatic solid tumours characterized by the
  a) administration of 300 mg of Volasertib or a pharmaceutically acceptable salt thereof or a hydrate thereof at one day within a 14, 15, 16, 17, 18, 19, 20, 21, 22, 23, 24, 25, 26, 27, 28, 29, 30 or 31 day treatment cycle and
  b) administration of 100 mg/m² BSA of Cisplatin at one day within the same treatment cycle
to a patient suffering from advanced and/or metastatic solid tumours (dosage schedule II).

Another object of the invention relates to a method of treating patients suffering from advanced and/or metastatic solid tumours characterized by the
  a) administration of 300 mg of Volasertib or a pharmaceutically acceptable salt thereof or a hydrate thereof at one day within a 14, 15, 16, 17, 18, 19, 20, 21, 22, 23, 24, 25, 26, 27, 28, 29, 30 or 31 day treatment cycle and
  b) administration of 75 mg/m² BSA of Cisplatin at one day within the same treatment cycle to a patient suffering from advanced and/or metastatic solid tumours (dosage schedule III).

Another object of the invention relates to a method of treating patients suffering from advanced and/or metastatic solid tumours characterized by the
  a) administration of 350 mg of Volasertib or a pharmaceutically acceptable salt thereof or a hydrate thereof at one day within a 14, 15, 16, 17, 18, 19, 20, 21, 22, 23, 24, 25, 26, 27, 28, 29, 30 or 31 day treatment cycle and
  b) administration of 100 mg/m² BSA of Cisplatin at one day within the same treatment cycle
  to a patient suffering from advanced and/or metastatic solid tumours (dosage schedule IV).

Another object of the invention relates to a method of treating patients suffering from advanced and/or metastatic solid tumours characterized by the
  a) administration of 350 mg of Volasertib or a pharmaceutically acceptable salt thereof or a hydrate thereof at one day within a 14, 15, 16, 17, 18, 19, 20, 21, 22, 23, 24, 25, 26, 27, 28, 29, 30 or 31 day treatment cycle and
  b) administration of 75 mg/m² BSA of Cisplatin at one day within the same treatment cycle
  to a patient suffering from advanced and/or metastatic solid tumours (dosage schedule V).

Another object of the invention relates to a method of treating patients suffering from advanced and/or metastatic solid tumours characterized by the
  a) administration of 300 to 500 mg, preferably 300 or 350 mg of Volasertib or a pharmaceutically acceptable salt thereof or a hydrate thereof at one day within a 14, 15, 16, 17, 18, 19, 20, 21, 22, 23, 24, 25, 26, 27, 28, 29, 30 or 31 day treatment cycle and
  b) administration of Carboplatin at a dose targeting AUC (area under the concentration versus time curve)=4 mg·min/mL to AUC=6 mg·min/mL at one day within the same treatment cycle
  to a patient suffering from advanced and/or metastatic solid tumours (dosage schedule VI).

Another object of the invention relates to a method of treating patients suffering from advanced and/or metastatic solid tumours characterized by the
  a) administration of 300 mg of Volasertib or a pharmaceutically acceptable salt thereof or a hydrate thereof at one day within a 14, 15, 16, 17, 18, 19, 20, 21, 22, 23, 24, 25, 26, 27, 28, 29, 30 or 31 day treatment cycle and
  b) administration of Carboplatin at a dose targeting AUC=6 mg·min/mL at one day within the same treatment cycle
  to a patient suffering from advanced and/or metastatic solid tumours (dosage schedule VII).

Another object of the invention relates to a method of treating patients suffering from advanced and/or metastatic solid tumours characterized by the
  a) administration of 300 mg of Volasertib or a pharmaceutically acceptable salt thereof or a hydrate thereof at one day within a 14, 15, 16, 17, 18, 19, 20, 21, 22, 23, 24, 25, 26, 27, 28, 29, 30 or 31 day treatment cycle and
  b) administration of Carboplatin at a dose targeting AUC=5 mg·min/mL at one day within the same treatment cycle
  to a patient suffering from advanced and/or metastatic solid tumours (dosage schedule VIII).

Another object of the invention relates to a method of treating patients suffering from advanced and/or metastatic solid tumours characterized by the
  a) administration of 350 mg of Volasertib or a pharmaceutically acceptable salt thereof or a hydrate thereof at one day within a 14, 15, 16, 17, 18, 19, 20, 21, 22, 23, 24, 25, 26, 27, 28, 29, 30 or 31 day treatment cycle and
  b) administration of Carboplatin at a dose targeting AUC=6 mg·min/mL at one day within the same treatment cycle
  to a patient suffering from advanced and/or metastatic solid tumours (dosage schedule IX).

Another object of the invention relates to a method of treating patients suffering from advanced and/or metastatic solid tumours characterized by the
  a) administration of 350 mg of Volasertib or a pharmaceutically acceptable salt thereof or a hydrate thereof at one day within a 14, 15, 16, 17, 18, 19, 20, 21, 22, 23, 24, 25, 26, 27, 28, 29, 30 or 31 day treatment cycle and
  b) administration of Carboplatin at a dose targeting AUC=5 mg·min/mL at one day within the same treatment cycle
  to a patient suffering from advanced and/or metastatic solid tumours (dosage schedule X).

For all of the above given dosage schedules, the preferred treatment cycles are 14, 21 or 28 day per treatment cycle, more preferably it is a 21 day treatment cycle. Volasertib and Cisplatin or Volasertib and Carboplatin can be administered at the same day or at different days during the treatment cycle. Preferably the compounds are administered at the same day. Preferably the compounds are administered at the same time or consecutively with a short break (about 30 min) between the administrations. For example, as first medicament Cisplatin or Carboplatin is administered and after a 30 min break between the end of the administration of Cisplatin or Carboplatin Volasertib is administered.

The primary determinant of carboplatin clearance is glomerular filtration rate (GFR). GFR is a parameter of the renal function and is often decreased in elderly patients. Dosing formulas incorporating estimates of GFR to provide predictable carboplatin plasma AUCs should be used, especially in elderly patients, to minimize the risk of toxicity.

The dosing of carboplatin by target AUC is described in the current drug label. A simple formula for calculating dosage, based upon a patients glomerular filtration rate (GFR in mL/min) and carboplatin injection target area under the concentration versus time curve (AUC in mg/mL·min), has been proposed by Calvert Based on the Calvert formula, the Carboplatin doses can be calculated as:

$$\text{Total Carboplatin Dose (mg)} = (\text{target AUC}) \times (\text{GFR} + 25) \quad [\text{Calvert formula}]$$

If a patient's GFR is estimated based on serum creatinine measurements by the IDMS (Isotope Dilution Mass Spectrometry) method, FDA recommends that physicians consider capping the dose of carboplatin for desired exposure (AUC) to avoid potential toxicity due to overdosing as follows:

The maximum dose is based on a GFR estimate that is capped at 125 mL/min for patients with normal renal function. No higher estimated GFR values should be used.

For a target AUC=6, the maximum dose is 6×150=900 mg
For a target AUC=5, the maximum dose is 5×150=750 mg
For a target AUC=4, the maximum dose is 4×150=600 mg Another object of the invention refers to Volasertib or a pharmaceutically acceptable salt thereof or a hydrate thereof for the use in treating advanced and/or metastatic solid tumours in patients suffering from advanced and/or metastatic solid tumours characterized in that Volasertib or a pharmaceutically acceptable salt thereof or a hydrate thereof is administered according to one of the dosage schedules I to X.

Another object of the invention refers to Cisplatin for the use in treating advanced and/or metastatic solid tumours in patients suffering from advanced and/or metastatic solid tumours characterized in that Cisplatin is administered according to one of the dosage schedules I to X.

Another object of the invention refers to Carboplatin for the use in treating a advanced and/or metastatic solid tumours in patients suffering from advanced and/or metastatic solid tumours characterized in that Carboplatin is administered according to one of the dosage schedules I to X.

Another object of the invention refers to the use of Volasertib or a pharmaceutically acceptable salt thereof or a hydrate thereof for the manufacture of a medicament for treating advanced and/or metastatic solid tumours in patients suffering from advanced and/or metastatic solid tumours wherein the medicament is prepared for administration according to one of the dosage schedules I to X.

Another object of the invention refers to the use of Cisplatin or a pharmaceutically acceptable salt thereof or a hydrate thereof for the manufacture of a medicament for treating advanced and/or metastatic solid tumours in patients suffering from advanced and/or metastatic solid tumours wherein the medicament is prepared for administration according to one of the dosage schedules I to X.

Another object of the invention refers to the use of Carboplatin or a pharmaceutically acceptable salt thereof or a hydrate thereof for the manufacture of a medicament for treating advanced and/or metastatic solid tumours in patients suffering from advanced and/or metastatic solid tumours wherein the medicament is prepared for administration according to one of the dosage schedules I to X.

Another object of the invention is a pharmaceutical composition comprising an effective amount of Volasertib and an effective amount of Cisplatin together with an instruction for administration of both active ingredients to a patient suffering from advanced and/or metastatic tumours, wherein according to said instruction Volasertib and/or Cisplatin is to be administered according to the above mentioned dosage schedules I to X.

Another object of the invention is a pharmaceutical composition comprising an effective amount of Volasertib and an effective amount of Carboplatin together with an instruction for administration of both active ingredients to a patient suffering from advanced and/or metastatic tumours, wherein according to said instruction Volasertib and/or Carboplatin is to be administered according to the above mentioned dosage schedules I to X.

Another object of the invention is a pharmaceutical composition comprising an effective amount of Volasertib together with an instruction for administration of Volasertib and Cisplatin to a patient suffering from advanced and/or metastatic tumours, wherein according to said instruction Volasertib and Cisplatin is to be administered according to the above mentioned dosage schedules I to X.

Another object of the invention is a pharmaceutical composition comprising an effective amount of Volasertib a together with an instruction for administration of Volasertib and Carboplatin to a patient suffering from advanced and/or metastatic tumours, wherein according to said instruction Volasertib and Carboplatin is to be administered according to the above mentioned dosage schedules I to X.

Another object of the invention is a pharmaceutical kit, comprising a first compartment which comprises an effective amount of Volasertib and a second compartment which comprises an effective amount of Cisplatin, together with an instruction for administration of both active ingredients to a patient suffering from advanced and/or metastatic tumours, wherein according to said instruction Volasertib and Cisplatin is to be administered according to one of the above mentioned dosage schedules I to X.

Another object of the invention is a pharmaceutical kit, comprising a first compartment which comprises an effective amount of Volasertib and a second compartment which comprises an effective amount of Carboplatin, together with an instruction for administration of both active ingredients to a patient suffering from advanced and/or metastatic tumours, wherein according to said instruction Volasertib and Carboplatin is to be administered according to one of the above mentioned dosage schedules I to X.

This treatment cycle can be repeated as long as patients are eligible for repeated cycles, i.e. until progression of disease, or unacceptable toxicity and as long as neither patient nor investigator requests treatment discontinuation. If platinum treatment needs to be stopped the patient might be switched to Volasertib monotherapy The instruction for administration may be in any form suitable for pharmaceuticals, e.g. in form of a leaflet added to the dosage form within secondary packaging or an imprint on the primary or secondary packaging.

Dosages/Volasertib:

For intraveneous treatment Volasertib may be administered to the human patient in a daily dose of 300 to 500 mg/application, preferably 300 or 350 mg/application. For instance, Volasertib can be administered as a slow intravenous infusion over several hours, e.g. over about 1, 2, 4, 6, 10, 12 or 24 hours, preferably about 1 or 2 hours.

However, it may optionally be necessary to deviate from the dosage amounts specified for Volasertib, depending on the body weight or method of administration, the individual response to the medication, the nature of the formulation used and the time or interval over which it is administered. Thus, in some cases, it may be sufficient to use less than the minimum quantity specified above, while in other cases the upper limit specified will have to be exceeded. When large amounts are administered it may be advisable to spread them over the day in a number of single doses.

Dosage Forms and Formulation Aspects

Regarding any aspects of the invention for Volasertib pharmaceutically acceptable salts or hydrates thereof may be used, preferably trihydrochloride salt forms and hydrates thereof as disclosed in WO 07/090844. Dosages or amounts of the actives provided in the context of this invention refer in any case to the free base equivalent, that is Volasertib in the free base form.

The term "therapeutically effective amount" shall mean that amount of a drug or pharmaceutical agent that will elicit the biological or medical response of a tissue system, animal or human that is being sought by a researcher or clinician, resulting in a beneficial effect for at least a statistically significant fraction of patients, such as a improvement of symptoms, a cure, a reduction in disease load, reduction in tumor mass, extension of life, or improvement in quality of life. For Volasertib the therapeutically effective amount within the meaning of the present invention is between 300 and 500 mg per day of administration. For Cisplatin the therapeutically effective amount within the meaning of the present invention is between 50 and 100 mg/m² BSA per day of administration. For Cisplatin the therapeutically effective amount within the meaning of the present invention is between 50 and 100 mg/m² BSA per day of administration. For Carboplatin the therapeutically effective amount within the meaning of the present invention is calculation according to the Calvert formula:

$$\text{Total Carboplatin Dose (mg)} = (\text{target AUC}) \times (\text{GFR} + 25) [\text{Calvert formula}].$$

Day 1 of a e.g. 21 day treatment cycle is defined as that day at which the first dose of Volasertib is administered.

The term "advanced and/or metastatic solid tumours" is defined as histologically or cytologically confirmed diagnosis of advanced, non resectable and/or metastatic relapsed or refractory solid malignant tumour, not amenable to standard therapy or for which no therapy of proven efficacy exists.

In accordance with the present invention Volasertib, Cisplatin and Carboplatin may be administered by parenteral (e.g. intramuscular, intraperitoneal, intravenous, transdermal or subcutaneous injection), preferably intravenous application, and may be formulated, alone or together, in suitable dosage unit formulations containing conventional non-toxic pharmaceutically acceptable carriers, adjuvants and vehicles appropriate for each route of administration. Dosage forms and formulations of both actives suitable within the present invention are known in the art. For instance, such dosage forms and formulations include those disclosed for Volasertib in WO 2006/018221.

The following Examples serve to illustrate the invention without restricting it:

EXAMPLE 1

Clinical Trial

Sequential cohorts of three to six patients (pts) received a single 2-hour infusion of Volasertib (V) in combination with Cisplatin (Cis) (arm A) or Carboplatin (Ca) (arm B), on day 1 every 3 weeks. Cis and Ca were given for up to six cycles (Cy), V was continued until disease progression or unacceptable toxicity.

Results:

46 patients have received Volasertib in combination with either Cisplatin or Carboplatin. The maximum tolerated dose for volasertib in combination with cisplatin or carboplatin in patients with advanced and/or metastatic solid tumours was at or above 300 mg. Patients have received between one and 16 cycles of treatment with volasertib, with a median (range) of three (one, six) cycles in combination with cisplatin and two (one, six) cycles in combination with carboplatin Efficacy Four partial responses (PR) have been observed: two in patients with CHOP-resistant follicular dendritic reticulum cell sarcoma in arm A (dose level [DL] A2, A4), one in a heavily-pretreated head and neck carcinoma in arm B (DL B4), and one in a patient with pretreated lung cancer (DL A5)
  one patient with dendritic reticulum cell sarcoma (DL A2) achieved a PR, remaining on treatment until discontinuation at the end of cycle 15 due to progressive disease (PD)
  another patient with dendritic reticulum cell sarcoma (DL A4; volasertib dose reduced to 200 mg from fifth cycle onwards due to febrile neutropenia) had stable disease (SD) at first evaluation and relevant tumor shrinkage at second evaluation. This patient achieved PR at cycle 4, and remains on treatment in cycle 16
  one patient with hypopharynx carcinoma (DL B4; volasertib dose reduced to 200 mg in cycle 2 due to DLT in cycle 1) achieved a PR in cycle 2, which was confirmed in cycle 4. The patient continues to have PR in cycle 12
  one patient with lung adenocarcinoma (DL A5) is receiving treatment in cycle 4 having achieved a PR in cycle 2 that has yet to be confirmed.

These results demonstrate the beneficial effect of the combined administration of Volasertib and Cisplatin or Volasertib and Carboplatin according to the dosage schedules I to X.

The invention claimed is:

1. A method of treating advanced and/or metastatic solid tumours, comprising administering 300 to 500 mg Volasertib or a pharmaceutically acceptable salt thereof or a hydrate thereof to a patient at one day during a 14, 15, 16, 17, 18, 19, 20, 21, 22, 23, 24, 25, 26, 27, 28, 29, 30 or 31 day treatment cycle in combination with
   b) 50 to 100 mg/m$^2$ BSA of Cisplatin at one day within the same treatment cycle or Carboplatin at a dose targeting AUC=4 mg·min/mL to AUC=6 mg·min/mL at one day within the same treatment cycle, to a patient suffering from advanced or metastatic solid tumours.

2. The method according to claim 1, comprising administering a dosage schedule (I) comprising or consisting of
   a) 300 to 500 mg of Volasertib or a pharmaceutically acceptable salt thereof or a hydrate thereof at one day within a 14, 15, 16, 17, 18, 19, 20, 21, 22, 23, 24, 25, 26, 27, 28, 29, 30 or 31 day treatment cycle and
   b) 50 to 100 mg/m2 BSA of Cisplatin at one day within the same treatment cycle, to a patient suffering from advanced or metastatic solid tumours.

3. The method according to claim 1, comprising administering a dosage schedule (I) comprising or consisting of
   a) 300 to 500 mg of Volasertib or a pharmaceutically acceptable salt thereof or a hydrate thereof at one day within a 14, 15, 16, 17, 18, 19, 20, 21, 22, 23, 24, 25, 26, 27, 28, 29, 30 or 31 day treatment cycle and
   b) Carboplatin at a dose targeting AUC=4 mg·min/mL to AUC=6 mg·min/mL at one day within the same treatment cycle,
   to a patient suffering from advanced or metastatic solid tumours.

4. The method according to claim 2 or 3, wherein the treatment cycle is 14, 21 or 28 days.

5. The method according to claim 2, wherein Volasertib and Cisplatin are administered at the same day.

6. The method according to claim 3, wherein Volasertib and Carboplatin are administered at the same day.

7. The method according to claim 5, wherein Volasertib and Cisplatin are administered at the same time.

8. The method according to claim 6, wherein Volasertib and Carboplatin are administered at the same time.

* * * * *